United States Patent
Shodo (10) Patent No.: US 7,941,222 B2
(45) Date of Patent: May 10, 2011

(54) VISION REGENERATION ASSISTING APPARATUS

(75) Inventor: Kenzo Shodo, Kyoto (JP)

(73) Assignee: Nidek Co., Ltd., Aichi (JP)

( * ) Notice: Subject to any disclaimer, the term of this patent is extended or adjusted under 35 U.S.C. 154(b) by 504 days.

(21) Appl. No.: 12/022,374

(22) Filed: Jan. 30, 2008

(65) Prior Publication Data

US 2008/0183243 A1    Jul. 31, 2008

(30) Foreign Application Priority Data

Jan. 30, 2007    (JP) ................ P.2007-020117

(51) Int. Cl.
*A61N 1/02*    (2006.01)
(52) U.S. Cl. .......................................... 607/54
(58) Field of Classification Search ........... 607/53–54
See application file for complete search history.

(56) References Cited

U.S. PATENT DOCUMENTS

| 6,920,361 B2* | 7/2005 | Williams ............... 607/122 |
| 7,242,597 B2 | 7/2007 | Shodo |
| 2002/0038134 A1* | 3/2002 | Greenberg et al. ........ 607/1 |
| 2006/0036295 A1 | 2/2006 | Greenberg et al. |
| 2006/0287688 A1* | 12/2006 | Yonezawa ............... 607/54 |
| 2007/0038267 A1 | 2/2007 | Shodo et al. |

FOREIGN PATENT DOCUMENTS

| EP | 1386636 A2 | 2/2004 |
| JP | 2006-050762 A | 2/2006 |
| JP | 2006-280410 A | 10/2006 |
| JP | 2006-280412 A | 10/2006 |
| JP | 2007-044323 A | 2/2007 |
| WO | 00/06248 A1 | 2/2000 |
| WO | WO 0006248 * | 2/2000 |

* cited by examiner

*Primary Examiner* — Scott M Getzow
*Assistant Examiner* — Amanda Patton
(74) *Attorney, Agent, or Firm* — Sughrue Mion, PLLC (57) ABSTRACT

A vision regeneration assisting apparatus for regenerating vision of a patient includes an extracorporeal device and an intracorporeal device. The extracorporeal device includes a transmitting unit that converts an electrical stimulation pulse signal data of image data and power into a predetermined signal and transmitting the signal. The intracorporeal device includes a receiving unit that receives the signal transmitted from the transmitting unit, and a conductor that is covered with a resin having biocompatibility and insulating property and electrically connects a first control unit for converting the received stimulation pulse signal data and the power into a predetermined alternating current signal and a second control unit for outputting an electrical stimulation pulse signal from electrodes based on the alternating current signal to each other to send the alternating current signal.

3 Claims, 5 Drawing Sheets

| Characteristics of Electrode | | | Limit Frequency kHz (E = 15 V) | | | |
|---|---|---|---|---|---|---|
| Frequency: 100 Hz to 1 MHz | | | When Charge Amount is 50 µC/cm² | | When Charge Amount is 400 µC/cm² | |
| Electrode | R[kΩ] | C[nF] | Sine Wave | Square Wave | Sine Wave | Square Wave |
| 1 | 3.5 | 19 | 86 | 132 | 11 | 16 |
| 2 | 3.3 | 18 | 91 | 139 | 11 | 17 |
| 3 | 3.2 | 17 | 96 | 146 | 12 | 18 |
| 4 | 7.6 | 19 | 40 | 61 | 5 | 8 |
| 5 | 8.7 | 21 | 35 | 54 | 4 | 7 |
| 6 | 7.9 | 19 | 38 | 59 | 5 | 7 |
| 7 | 1.9 | 24 | 162 | 249 | 20 | 31 |
| 8 | 1.7 | 21 | 177 | 271 | 22 | 34 |
| 9 | 1.6 | 19 | 188 | 288 | 24 | 36 |
| 10 | 1.6 | 18 | 191 | 292 | 24 | 36 |
| 11 | 1.5 | 22 | 200 | 307 | 25 | 38 |
| 12 | 1.5 | 20 | 198 | 304 | 25 | 38 |
| Maximum Value | | | 200 | 307 | 25 | 38 |
| Average Value | | | 125 | 192 | 16 | 24 |

VISION REGENERATION ASSISTING APPARATUS

BACKGROUND OF THE INVENTION

1. Field of the Invention

This invention relates to a vision regeneration assisting apparatus for regenerating vision of a patient.

2. Description of the Related Art

Vision regeneration assisting apparatuses for regenerating lost vision of a blind patient by applying electrical stimulation (electrical stimulation pulse signal) to the cells forming the retina from an electrode placed in the body (eye) of the blind patient have been proposed. Such apparatuses have an extracorporeal device including an image pickup unit and an intracorporeal device including a stimulation unit provided with a multiple of electrodes disposed on a substrate.

In such apparatuses, various units are provided in the intracorporeal device for outputting the electrical stimulation pulse signal from the electrodes based on electrical stimulation pulse signal data from the extracorporeal device. Since it is preferable to reduce the size and the number of units to be directly placed in the eye of the patient, the units are separately placed at positions distant from one another in the body and electrically connected with one another by a conductor coated with a resin excellent in (having) biocompatibility and insulation property.

However, since the intracorporeal device is placed in the body for a long time, there is a fear that the conductor is exposed to and wetted by the bodily fluid to exert adverse influence on the living body.

SUMMARY OF THE INVENTION

A technological object of this invention is to provide a vision regeneration assisting apparatus capable of suppressing adverse influence otherwise exerted on a living body when a conductor electrically connecting units that are placed separately at positions distant from one another in a body is exposed to and wetted by a bodily fluid.

In order to solve the above-described problem, this invention is characterized by having the following structure.

(1) A vision regeneration assisting apparatus for regenerating vision of a patient, comprising:
an extracorporeal device and an intracorporeal device,
wherein the extracorporeal device includes
an image pickup unit,
a processing unit that converts image data obtained by the image pickup unit into electrical stimulation pulse signal data, and
a transmitting unit that converts the electrical stimulation pulse signal data and power into a predetermined signal and transmitting the signal, and
wherein the intracorporeal device includes
a receiving unit that receives the signal transmitted from the transmitting unit,
a first control unit that extracts the electrical stimulation pulse signal data and the power from the signal received by the receiving unit to convert the electrical stimulation pulse signal data and the power into a predetermined alternating current signal,
a second control unit that is provided separately at a position distant from the first control unit and outputs an electrical stimulation pulse signal from a plurality of electrodes based on the alternating current signal from the first control unit, and
a conductor that is covered with a resin having biocompatibility and insulating property and electrically connects the first control unit and the second control unit to each other to send the alternating current signal.

(2) The vision regeneration assisting apparatus according to (1), wherein the first control unit generates the electrical stimulation pulse signal based on the extracted electrical stimulation pulse signal data and converts the generated electrical stimulation pulse signal and the power into the alternating current signal.

(3) A vision regeneration assisting apparatus for regenerating vision of a patient, comprising:
an extracorporeal device and an intracorporeal device,
wherein the extracorporeal device includes
an image pickup unit,
a processing unit that converts image data obtained by the image pickup unit into electrical stimulation pulse signal data, and
a transmitting unit that converts the electrical stimulation pulse signal data and power into a predetermined signal and transmitting the signal,
wherein the intracorporeal device includes
a receiving unit that receives the signal transmitted from the transmitting unit,
a first control unit that extracts the electrical stimulation pulse signal data and the power from the signal received by the receiving unit to convert the electrical stimulation pulse signal data and the power into a predetermined alternating current signal,
a second control unit that is provided separately at a position distant from the first control unit and outputs an electrical stimulation pulse signal from a plurality of electrodes based on the alternating current signal from the first control unit, and
a conductor that is covered with a resin having biocompatibility and insulating property and electrically connects the first control unit and the second control unit to each other to send the alternating current signal, and
wherein a charge amount per half wave of the alternating current signal is set so that, when the conductor is exposed and wetted by bodily fluid, a charge amount per unit area discharged from the conductor does not cause electrical decomposition of the bodily fluid.

(4) The vision regeneration assisting apparatus according to (3), wherein the first control unit generates the electrical stimulation pulse signal based on the extracted electrical stimulation pulse signal data and converts the generated electrical stimulation pulse signal and the power into the alternating current signal.

(5) A vision regeneration assisting apparatus for regenerating vision of a patient, comprising:
an extracorporeal device and an intracorporeal device,
wherein the extracorporeal device includes
an image pickup unit,
a processing unit that converts image data obtained by the image pickup unit into electrical stimulation pulse signal data, and
a transmitting unit that converts the electrical stimulation pulse signal data and power into a predetermined signal and transmitting the signal,
wherein the intracorporeal device includes
a receiving unit that receives the signal transmitted from the transmitting unit,
a first control unit that extracts the electrical stimulation pulse signal data and the power from the signal received by the receiving unit to convert the electrical stimulation pulse signal data and the power into a predetermined alternating current signal, a second control unit that is provided separately at a position distant from the first control unit and outputs an electrical stimulation pulse signal from a plurality of electrodes based on the alternating current signal from the first control unit, and a conductor that is covered with a resin having biocompatibility and insulating property and electrically connects the first control unit and the second control unit to each other to send the alternating current signal, wherein the conductor being made from platinum or a platinum alloy, and wherein a charge amount per half wave of the alternating current signal is set so that, when the conductor is exposed and wetted by bodily fluid, a charge amount per unit area discharged from the conductor is 400 µC/cm² or less.

(6) The vision regeneration assisting apparatus according to (5), wherein the charge amount per half wave of the alternating current signals is set so that, when the conductor is exposed and wetted by the bodily fluid, the charge amount per unit area discharged from the conductor is 50 µC/cm² or less.

(7) The vision regeneration assisting apparatus according to (5), wherein the first control unit generates the electrical stimulation pulse signal based on the extracted electrical stimulation pulse signal data and converts the generated electrical stimulation pulse signal and the power into the alternating current signal.

DESCRIPTION OF THE PREFERRED EMBODIMENTS

Figure 1:
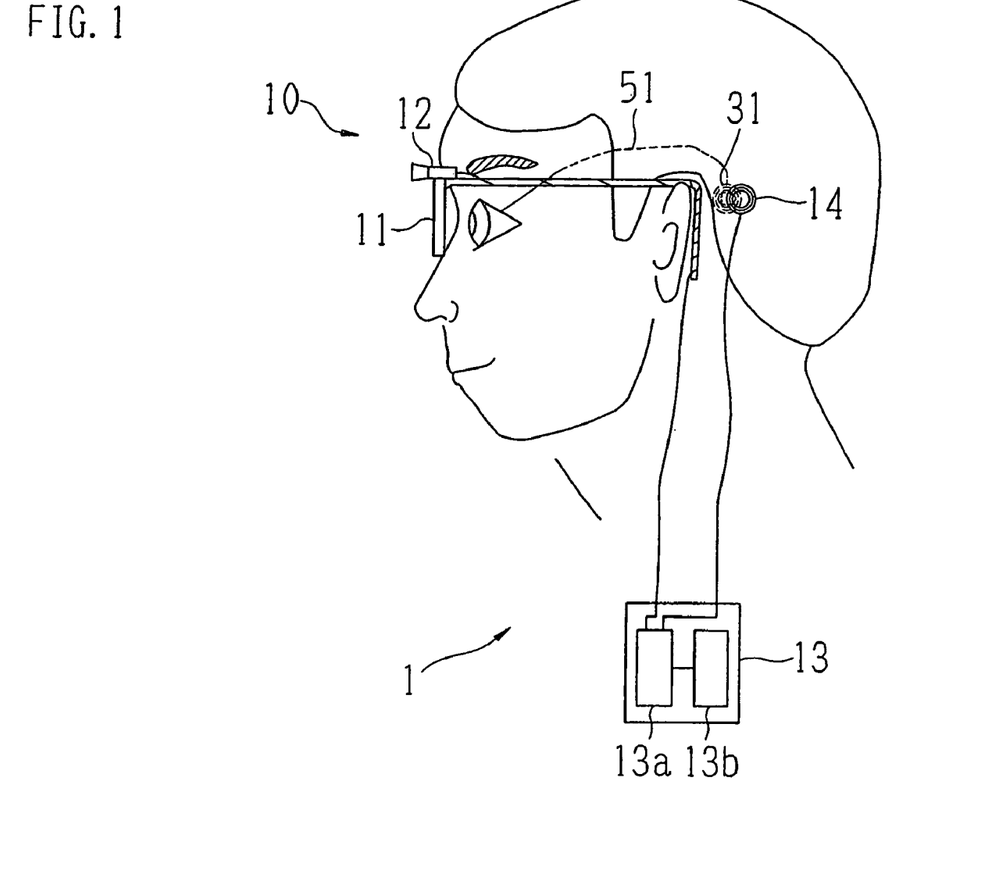
FIG. 1 is a schematic diagram showing an extracorporeal device of a vision regeneration assisting apparatus according to one embodiment of this invention.
Figure 2A:
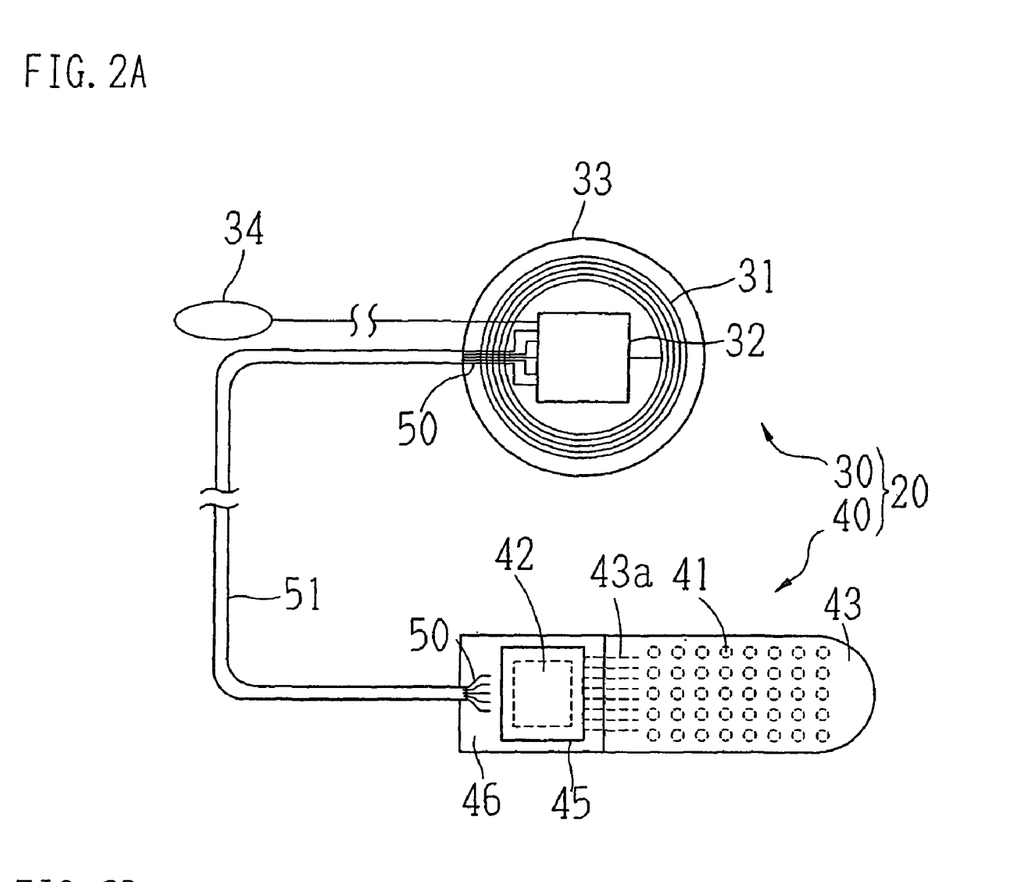
FIG. 2A and FIG. 2B are schematic diagrams showing an intracorporeal device of the vision regeneration assisting apparatus.
Figure 2B:
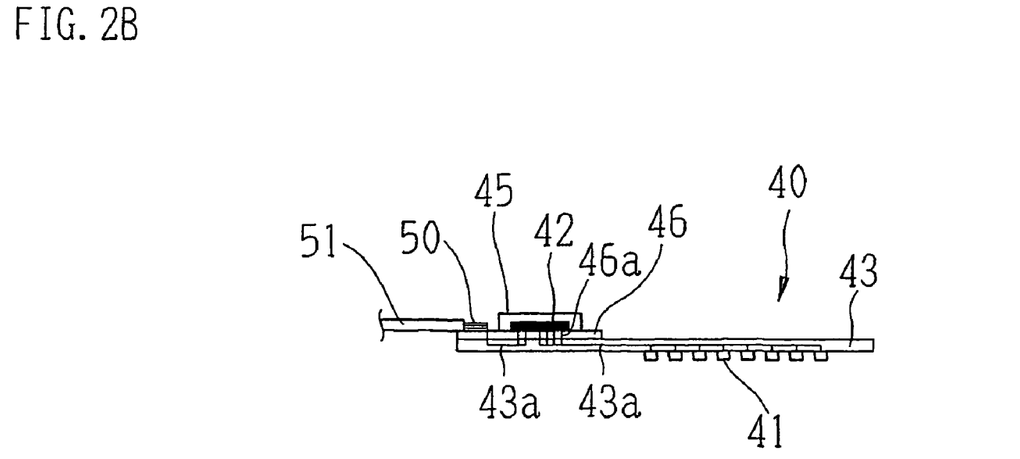

This invention will be described based on the drawings. FIG. 1 is a schematic diagram showing an extracorporeal device 10 of a vision regeneration assisting apparatus 1 according to one embodiment of this invention. FIGS. 2A and 2B are schematic diagrams showing an intracorporeal device 20 of the apparatus 1, FIG. 2A is a plan view showing the intracorporeal device 20 as viewed from one side that is opposite to electrode arrangement, and FIG. 2B is a sectional view showing the intracorporeal device 20 as viewed from one side with the side of the electrode arrangement facing in a downward direction.

The extracorporeal device 10 includes a visor 11 for a patient to wear, an image pickup unit 12 formed of a CCD camera and the like attached to the visor 11, an external unit 13, and a transmitting unit 14 including a primary coil.

The visor 11 has the shape like glasses and is used as being attached in front of the eyes of the patient. The image pickup unit 12 is attached to a front surface of the visor 11 and picks up an object to be visually recognized by the patient.

The external unit 13 includes a processing unit (signal conversion unit) 13a having an arithmetic processing circuit such as a CPU and a power source unit (battery) 13b for supplying power to the apparatus 1 (extracorporeal device 10 and intracorporeal device 20). The processing unit 13a performs image processing of image data obtained by the image pickup unit 12 to convert the image data into electrical stimulation pulse signal data.

The transmitting unit 14 transmits the electrical stimulation pulse signal data obtained by the conversion and the power (power data) from the power source unit 13b via the processing unit 13a to the intracorporeal device 20 as electromagnetic waves. The electromagnetic waves have a frequency of about 16 MHz and are transmitted/received by frequency modulation. At the center of the transmitting unit 14, a magnet (not shown) is attached to be used for improving data transmitting efficiency by the transmitting unit 14 and position fixation of a receiving unit 31 described below.

The intracorporeal device 20 includes an internal unit 30 for receiving the electrical stimulation pulse signal data and the power transmitted from the extracorporeal device 10 and a stimulation unit 40 for applying electrical stimulation to the cells forming the retina.

The internal unit 30 includes the receiving unit 31 including a secondary coil for receiving the electrical stimulation pulse signal data and the power transmitted from the transmitting unit 14 as the electromagnetic waves and a control unit 32. The control unit 32 separates the electromagnetic waves received by the receiving unit 31 into the electrical stimulation pulse signal data and the power and obtains a control signal (electrode assignment signal, etc.) and a parameter signal (intensity signal, etc.) of an electrical stimulation pulse signal based on the electrical stimulation pulse signal data, thereby generating the electrical stimulation pulse signal.

The receiving unit 31 and the control unit 32 are made from a metal or the like excellent in (having) biocompatibility and disposed on a substrate 33. At the center of the receiving unit 31, a magnet (not shown) is attached to be used for improving data transmitting efficiency by the receiving unit 31 and position fixation of the transmitting unit 14.

The stimulation unit 40 includes a plurality of electrodes 41 for outputting the electrical stimulation pulse signal and a control unit 42. The control unit 42 distributes the electrical stimulation pulse signals to the electrodes based on the control signal from the control unit 32 to output the electrical stimulation pulse signals to the cells forming the retina. The electrical stimulation pulse signals outputted from the electrodes 41 are two-phase (dipolar) pulse signals that are alternating current signals.

The electrodes 41 are made from a metal excellent in (having) biocompatibility and electroconductivity, such as gold, platinum, titanium nitride, and iridium oxide, and formed (disposed) on a substrate 43. Since it is preferable that the substrate 43 fits to the shape of the eye ball so as to be placed in the eye, particularly in the eye tissue which is in a layered form, the substrate 43 is made from a resin excellent in biocompatibility and capable of being curved at a predetermined thickness, such as polypropylene and polyimide, and has a rectangular shape. A thickness of the substrate 43 may preferably be about 50 µm, so that a certain degree of strength and flexibility are maintained. A conductor 43a is formed on (in) the substrate 43, so that the electrodes 41 and the control unit 42 are electrically connected to each other.

The control unit 42 is disposed on and attached to a base 46 and covered with a cover 45. The base 46 is made from a material excellent in (having) biocompatibility, sealing property, and insulating property and has a flat plate-like shape. A conductor 46a is formed on (in) the base 46, so that the electrodes 41 (conductor 43a) and the control unit 42 are electrically connected to each other. The cover 45 is made from a material excellent in (having) biocompatibility and sealing property and has a box-like shape (hat-like shape), the cover 45 being attached to the base by adhesion, welding, or the like. That is, the control unit 42 is hermetically sealed.

Though not shown, the control unit 32 is also hermetically sealed like the control unit 42.

The internal unit 30 and the stimulation unit 40 that are disposed at distant positions in the body are connected to each other by a plurality of conductors 50 (conductors 50a to 50d). The conductors 50 are made from a metal or the like excellent in (having) biocompatibility and electroconductivity, such as platinum, platiniridium, stainless and titanium. The conductors 50 are bundled by a tube 51 made from a resin excellent in (having) biocompatibility and insulating property, such as silicone and perylene, so that handling thereof is easy. Each of the conductors 50 is coated with a resin excellent in (having) biocompatibility and insulating property, such as silicone and perylene. Since the signals passing through the conductors 50 are the alternating current signals, it is possible to prevent adverse influence from being exerted on the living body even when the conductors 50 are exposed to and wetted by the bodily fluid.

Figure 3:
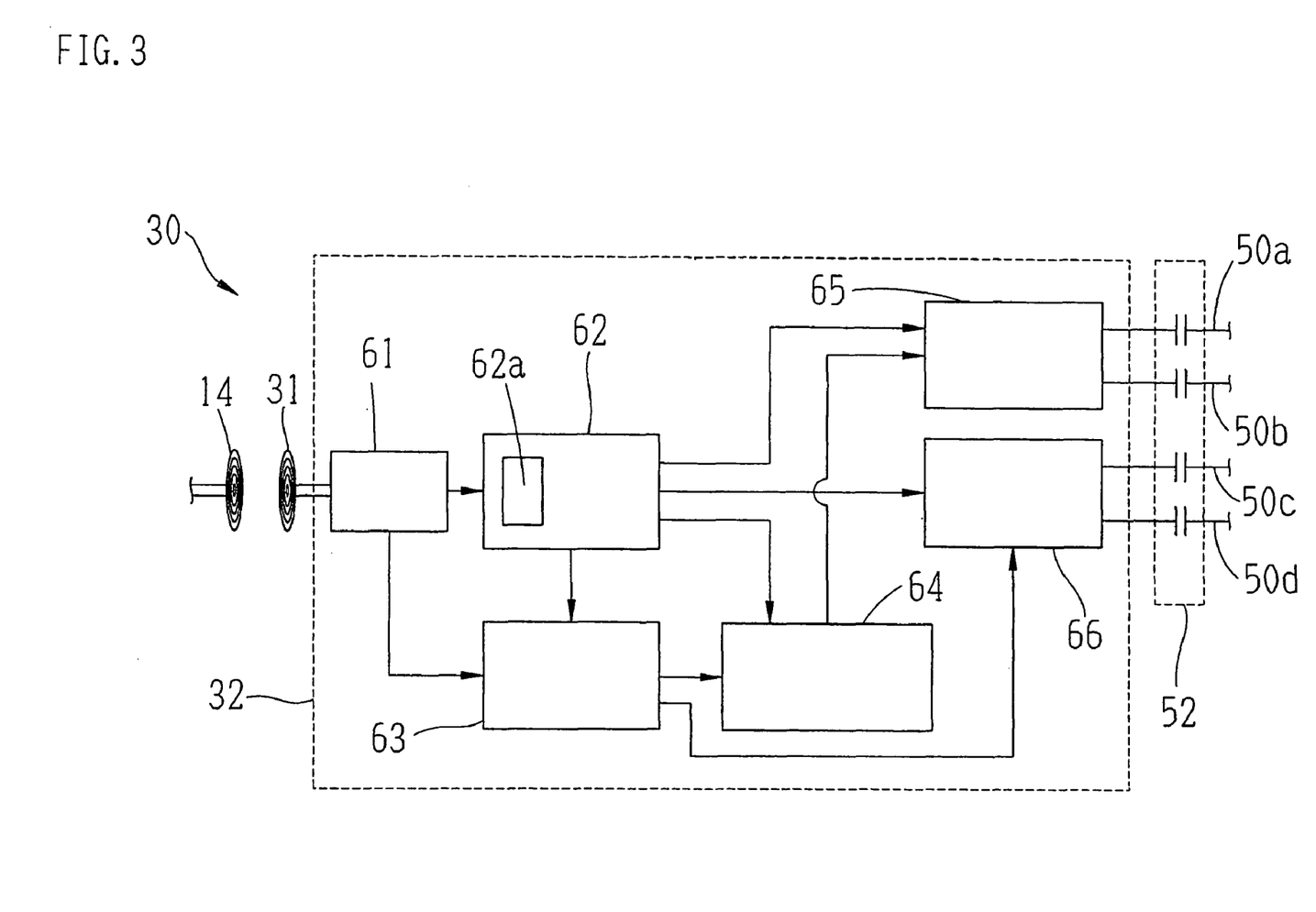
FIG. 3 is a schematic block diagram showing an internal structure of an internal unit.
Figure 4:
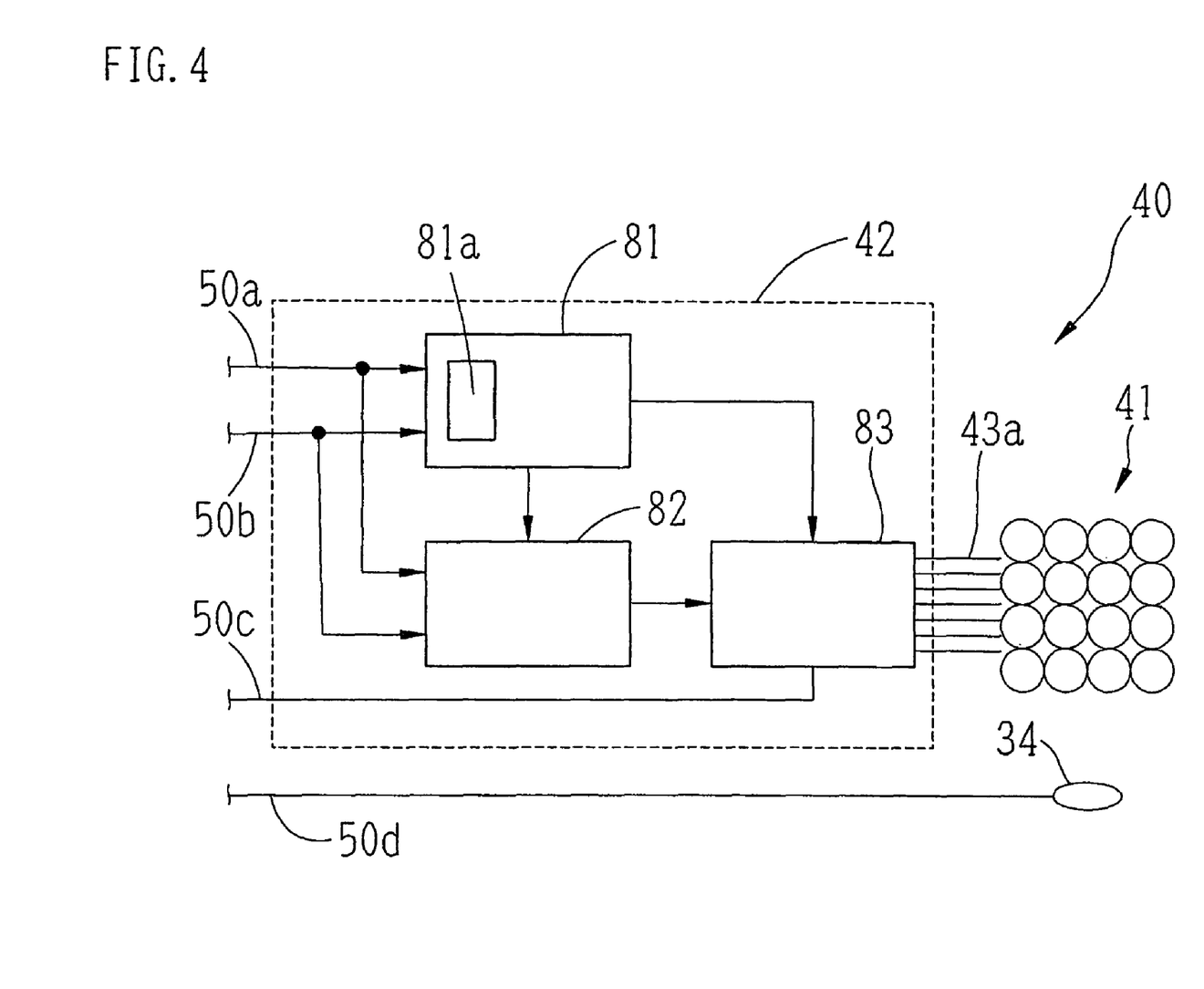
FIG. 4 is a schematic block diagram of an internal structure of a stimulation unit.

FIG. 3 is a schematic block diagram showing an internal structure of the internal unit 30, and FIG. 4 is a schematic block diagram showing an internal structure of the stimulation unit 40. In FIGS. 3 and 4, the blocks are units formed in a semiconductor integration circuit and execute functions by combinations of various semiconductor elements (transistor such as MOSFET, diode, resistance, condenser, etc.). Description of detailed circuit configuration and the like of each of the blocks is omitted.

The electromagnetic wave from the extracorporeal device 10 is transmitted as the alternating current signal via the transmitting unit 14 and the receiving unit 31 to a receiving block 61 that is connected to the receiving unit 31. The receiving block 61 separates the alternating current signal into the electrical stimulation pulse signal data and the power.

The separated power is transmitted to a power source block 62 connected to the receiving block 61. The power source block 62 converts the power transmitted as the alternating current signal into a direct current by a rectifier 62a and supplies the power of direct current voltage to a decoder 63, an encoder 64, a power supply block 65, and a stimulation block 66. The separated electrical stimulation pulse signal data are transmitted to the decoder 63 connected to the receiving block 61. The decoder 63 obtains the control signal and the parameter signal of the electrical stimulation pulse signal based on the transmitted electrical stimulation pulse signal data.

The obtained control signal is transmitted to the encoder 64 connected to the decoder 63. The encoder 64 overlaps the transmitted control signal on the alternating current signal by frequency modulation. The control signal overlapped on the alternating current signal by the encoder 64 is transmitted to the power supply block 65 connected to the encoder 64. The power supply block 64 uses the direct current voltage from the power source block 62 to amplify the alternating current signal on which the control signal is overlapped.

In turn, the obtained parameter signal is transmitted to the stimulation block 66 connected to the decoder 63. The stimulation block 66 generates the electrical stimulation pulse signal having predetermined intensity and sustain period based on the parameter signal and the direct current voltage (or current) transmitted from the power source block 62.

The conductors 50a and 50b which transmit positive and negative signals in alternating current transmission and are paired to each other are connected to the power supply block 65, and the conductors 50c and 50d which transmit positive and negative signals in alternating current transmission and are paired to each other are connected to the stimulation block 66. A coupling condenser 52 having a role of a filter for blocking the direct current signals and passing only the alternating current signals is connected to an intermediate point of each of the conductors 50a to 50d. The number of each of the conductors 50a to 50b may be two or more.

In order to prevent adverse influence from being exerted on the living body even when the conductors 50 are exposed to and wetted by the bodily fluid, the upper limit value of a charge amount per half wave of the alternating current signals passing through the conductors 50 (transmitted by the conductors 50) is so set that a charge amount (charge density) per unit area of an exposure part (wetted part) of the conductors 50 is kept to a value that does not cause electrical decomposition of the bodily fluid, and the threshold value of the frequency is set based on the threshold value of the charge amount. The frequency of the alternating current signal may preferably be about 20 kHz or more (more preferably about 200 kHz or more) in the case of sine wave since the electrical stimulation pulse signal outputted from the electrodes 41 is from several voltages to several tens of voltages. The frequency of the alternating current signal in the case of square wave may preferably be about 40 kHz or more (more preferably about 300 kHz or more) for the same reason. Also, the upper limit value of the frequency of the alternating current signal is set to a value that keeps noise generated from the intracorporeal device 20 within an acceptable range.

The conductors 50a, 50b, and 50c are connected to the control unit 42, and the conductor 50d is connected to an opposite electrode 34. The conductors 50a and 50b are connected in parallel to a power source block 81 and a decoder 82 of the control unit 42. The power source block 81 converts the alternating current signal from the power source block 65 into the direct current signal by a rectifier 81a to supply the power of direct current voltage to the decoder 82 and a multiplexer 83. The decoder 82 extracts the control signal from the alternating current signal to transmit the control signal to the multiplexer 83.

The multiplexer 83 is connected to the decoder 82 and the stimulation block 66 via the conductor 50c and further connected to the electrodes 41 via the conductor 43a. The multiplexer 83 distributes the electrical stimulation pulse signal from the stimulation block 66 to the electrodes 41 based on the control signal from the decoder 82.

Hereinafter, a method for deciding each threshold value of the charge amount per half wave and the frequency of the alternating current signal that do not cause adverse influence to be exerted on the living body, i.e. do not cause the bodily fluid to be electrically decomposed at an exposure part (wetted part) of the conductors 50, according to this embodiment will be described.

The charge amount per half wave of the alternating current signal passing through the conductors 50 and injected from a part at which the conductors 50 are exposed to and contact the bodily fluid will be detected. A condition for preventing adverse influence from being exerted on the living body at the contact part of the conductors 50 and the bodily fluid (exposure part of the conductors 50) is such that the charge amount per half wave of the alternating current signal is equal to or less than the upper limit value of the charge amount per unit area that does not cause electrical decomposition of the bodily fluid. The charge amount is obtained by an experiment and calculation.

As the experiment, in a state where an electrode having a certain surface area and made from the material same as that of the conductors 50 is dipped into a normal saline solution similar to the bodily fluid, an impedance between the electrode and an opposed electrode having a surface area satisfactorily larger than the electrode dipped into the same normal saline solution is measured. The electrode assumed to be the conductors 50 has a diameter of 200 μm and is made from platinum, and the impedance of the platinum electrode is demodeled by an RC serial circuit (a resistance component of the impedance is R, and a capacitance component of the impedance is C).

The charge amount per half wave of the alternating current signal is calculated as follows. When the frequency of the output voltage v of the power supply block 65 is represented by f, a peak voltage is represented by E, and a cycle is represented by T(1/f), and time is represented by t, v=E·sin (2πft) holds in the case of sine wave, and v=E holds in the case of square wave.

Accordingly, the charge amount Q per half wave (t=0 to T/2) when the current is represented by i in the case of sine wave is as indicated by Expression 1, and the charge amount Q in the case of square wave is as indicated by Expression 2.

$$Q = \int_0^{\frac{1}{2f}} i\,dt = \int_0^{\frac{1}{2f}} \frac{E\sin(2\pi ft)}{R + \frac{1}{j2\pi fC}}\,dt = \frac{j2CE}{1 + j2\pi fCR}$$

Expression 1

$$Q = \int_0^{\frac{1}{2f}} i\,dt = \int_0^{\frac{1}{2f}} \frac{E}{R}e^{-\frac{t}{CR}}\,dt = EC\left(1 - e^{-\frac{t}{2RF}}\right)$$

Expression 2

From Expressions 1 and 2, it is apparent that the charge amount Q tends to be decreased in accordance with an increase in frequency f in the case where the peak voltage E is a fixed value.

In general, the upper limit value of the charge amount per unit area that does not cause electrical decomposition of the bodily fluid when the electrode contacts the bodily fluid is decided depending on the material of the electrode and may preferably be about 400 μC/cm$^2$, more preferably 50 μC/cm$^2$, in the case of the platinum electrode. The upper limit value of the charge amount per unit area is multiplied by the area of the electrode used in the experiment to be converted into the charge amount, and the frequency f serving as the threshold value is obtained by assigning the charge amount to Expressions 1 and 2.

By the above calculations, the frequency in the case of using platinum as the material for the conductors is calculated as follows.

The surface area of the electrode having the diameter of 200 μm is 0.0314 mm$^2$ (314×10$^{-6}$ (cm$^2$)) by the experiment. With the impedance of the platinum electrode, the resistance component R was 1.5 kΩ, and the capacitance component C was 22 nF, for example. When the peak voltage E to be applied to the conductors is 15 V, the frequency f achieving the charge amount per unit area of 50 μC/cm$^2$ with which the bodily fluid is not electrically decomposed is 200 kHz from Expression 1 in the case of sine wave, and the frequency f in the case of square wave is 307 kHz from Expression 2.

Figure 5:
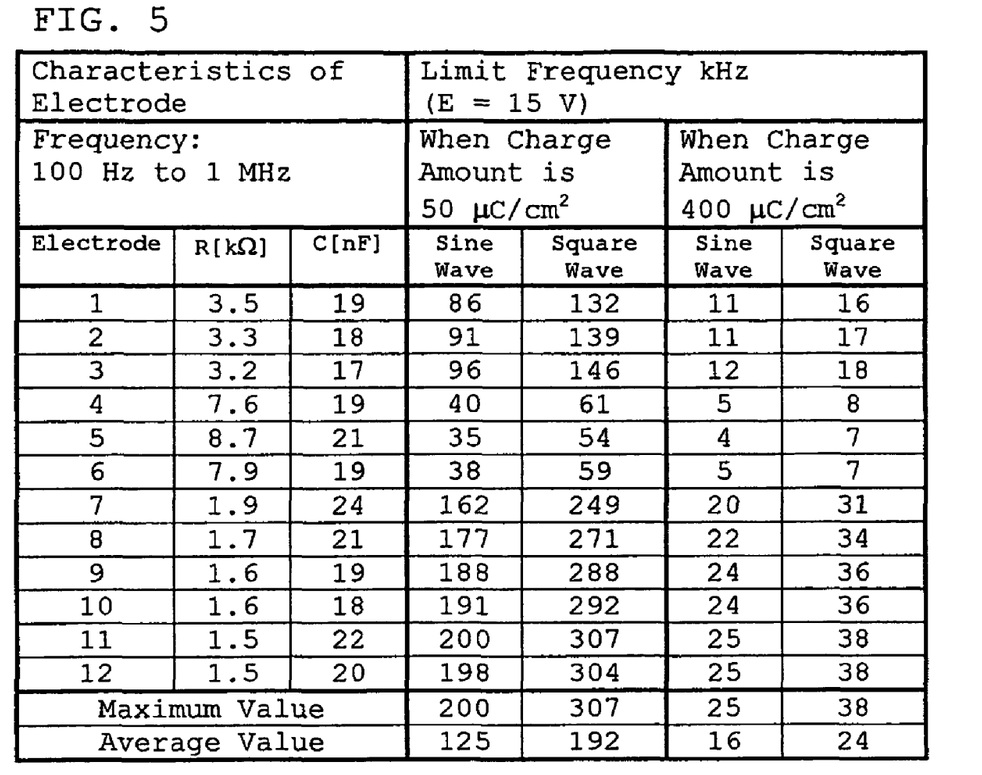
FIG. 5 is a diagram showing a relationship between a characteristic of a platinum electrode and each threshold value of a charge amount and a frequency of an alternating current signal.

FIG. 5 is a diagram showing results obtained by assigning the resistance component R and the capacitance component C of the platinum electrode to Expression 1 and Expression 2, wherein a relationship between the characteristic of the platinum electrode and each threshold value of the charge amount and the frequency of the alternating current signal are indicated. In the twelve platinum electrodes, the maximum value of frequencies when the threshold value of the charge amount per unit area was 50 μC/cm$^2$ was 200 kHz in the case of sine wave, and the maximum value of frequencies in the case of square wave was 307 kHz. Also, the average value of the frequencies in the case of sine wave was 125 kHz, and the average value of frequencies in the case of square wave was 192 kHz. Likewise, when the threshold value of the charge amount per unit area was 400 μC/cm$^2$, the maximum value of the frequencies in the case of sine wave was 25 kHz, and the maximum value of frequencies in the case of square wave was 38 kHz. The average value of the frequencies in the case of sine wave was 16 kHz, and the average value of the frequencies in the case of square wave was 24 kHz.

Consequently, when the frequency equal to or more than the threshold value is set to the lowest frequency of the alternating current signal (the lowest frequency in the case of frequency modulation), it is considered that the bodily fluid is not electrically decomposed even when the conductors 50 are exposed to and wetted by the bodily fluid. The frequency threshold values are set appropriately by experiment and the like. For example, the frequency threshold values may be set considering the average values of the frequencies.

In this embodiment, a standard frequency of the alternating current signal is about 1 MHz that is obtained by multiplying the obtained frequency threshold value by a satisfactory factor of safety (e.g. 2 or 3).

The threshold value of the charge amount per unit area that is considered to be safe for the living bodies means the value at which the bodily fluid is not electrically decomposed. The threshold value is not constant and changed depending on the material. In this embodiment, the case of using platinum as the material for the conductors is presumed, and the frequency threshold values were obtained based on the charge amount when platinum is used. However, when the material of the conductor is changed, the threshold value of the charge amount is changed, and the threshold value of the frequency is also changed. In such case, the threshold value of the charge amount may be set depending on the material of the conductors for calculating the threshold value of the frequency. Also, though the threshold value of the charge amount per unit area of the platinum conductor may preferably be about 400 μC/cm$^2$ (more preferably about 50 μC/cm$^2$), it is considered that a conductor made from an alloy of platinum, such as platinum iridium, has similar tendency (similarity).

Also, though the peak voltage to be applied to the conductors is the fixed value in the above calculations and the like, the peak voltage is not limited to the fixed value. Since the electrical stimulation pulse signal is generated from the alternating current signal of several voltages to several tens of voltages in order to electrically stimulate the cells forming the retina, any value capable of obtaining the alternating current signal of such voltage may be used. The charge amount of the alternating current signal, frequency, and the like are set to the values with which the bodily fluid is not electrically decomposed when the conductors are exposed to and wetted by the bodily fluid.

In order to reduce the size of the intracorporeal device 20, the control units 32 and 42 may preferably have a monolithic structure. The frequency of the alternating current signal passing through the platinum conductors may preferably be about 1 MHz which is about 2 to 3 times of the threshold value of the frequency in order to achieve the frequency appropriate for operation of the control unit 42 having the monolithic structure. When the frequency of the alternating current signal is low, it is necessary to use a condenser having a large capacity for a rectifying circuit (rectifier 81a) for obtaining stable power in the control unit 42, thereby increasing the size of the control unit 4. Also, when the frequency is high (for example exceeding 2 MHz), the conductor becomes a noise source.

Figure 6:
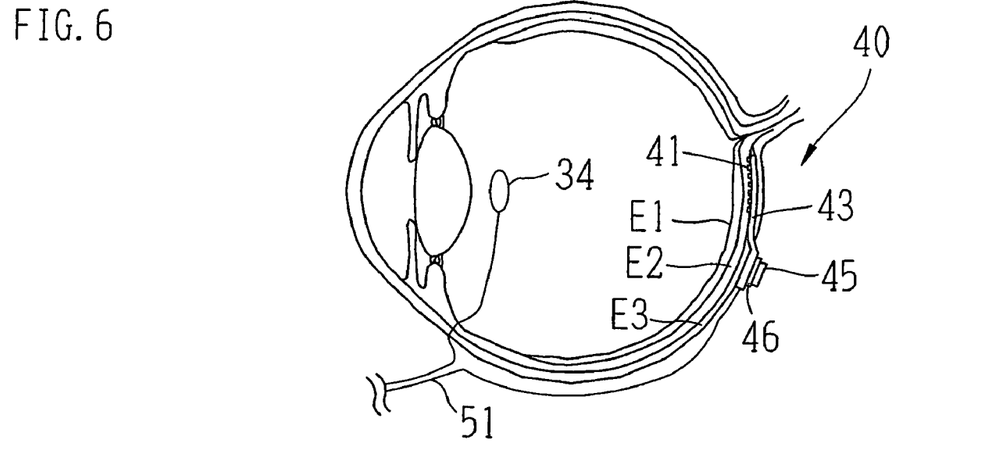
FIG. 6 is a diagram showing a state in which the stimulation unit is placed in a body.

FIG. 6 is a diagram showing a state in which the stimulation unit 40 is placed in a body (eye). The opposite electrode 34 is placed at a position near the anterior chamber side in the eye, and the electrodes 41 are placed at the chorioid E2 from the sclera E3. With such constitution, the retina E1 is defined between the electrodes 41 and the opposite electrode 34, and the electrical stimulation pulse signals from the electrodes 41 efficiently penetrate the retina 1E.

The internal unit 30 is placed at a predetermined position which is capable of receiving the signal from the transmitting unit 14 in a body of a patient. For example, the internal unit 30 is placed under the skin at the temporal part of the patient as shown in FIG. 1.

The tube 51 extends from the internal unit 30 toward the eye under the skin of the temporal part to be inserted into the eye hall and passed outside the sclera E3 to be connected to the control unit 42 provided on the substrate 43.

Though the electrodes are placed at the chorioid from the sclera side in this embodiment, the position is not limited to the above-described one, and it is possible to place the electrodes at any position capable of electrically stimulating the cells forming the retina. Also, the electrodes may be placed on the optic nerve papilla in the eye, the optic nerve outside the eye, or the like. The position of the substrate on which the electrodes are formed (disposed) is not limited to the chorioid, and it is possible to appropriately select the position that is reduced in load to be applied to the patient in view of the position at which the electrodes are placed. That is, this invention is applicable to those in which plural units of the intracorporeal device are connected via the conductor.

Though the modulation of the alternate current signal was performed by the frequency modulation in this embodiment, the modulation is not limited thereto, and it is possible to perform the modulation by amplification modulation or phase modulation. In the case of the frequency modulation, since amplitude of the alternating current signal is constant, it is possible to obtain substantially constant power when rectification is performed in the intracorporeal device (power source block).

What is claimed is:

1. A vision regeneration assisting apparatus for regenerating vision of a patient, the apparatus comprising:
    an extracorporeal device and an intracorporeal device,
    wherein the extracorporeal device includes:
        an image pickup unit,
        a processing unit that converts image data obtained by the image pickup unit into electrical stimulation pulse signal data, and
        a transmitting unit that converts the electrical stimulation pulse signal data and power into a predetermined signal and transmits the signal,
    wherein the intracorporeal device includes:
        a receiving unit that receives the signal transmitted from the transmitting unit,
        a first control unit that extracts the electrical stimulation pulse signal data and the power from the signal received by the receiving unit to convert the electrical stimulation pulse signal data and the power into a predetermined alternating current signal,
        a second control unit that is provided separately at a position distant from the first control unit and outputs an electrical stimulation pulse signal via a plurality of electrodes based on the alternating current signal from the first control unit, and
        a conductor that is covered with a resin having biocompatibility and insulating property and electrically connects the first control unit and the second control unit to each other to send the alternating current signal, and
    wherein the alternating current signal flowing through the conductor is set so that, when the conductor is exposed and wetted by bodily fluid, a charge amount per unit area discharged from the conductor does not cause electrical decomposition of the bodily fluid, and
    a frequency obtained from the following expressions is set as a lowest frequency of the alternating current signal:
    if a waveform of the alternating current signal is a sine wave, $$Q = \int_0^{\frac{1}{2f}} i\, dt = \int_0^{\frac{1}{2f}} \frac{E\sin(2\pi ft)}{R + \frac{1}{j2\pi fC}}\, dt = \frac{j2CE}{1 + j2\pi fCR}, \text{ or}$$

if the waveform of the alternating current signal is a square wave, $$Q = \int_0^{\frac{1}{2f}} i\, dt = \int_0^{\frac{1}{2f}} \frac{E}{R} e^{\frac{t}{CR}}\, dt = EC\left(1 - e^{\frac{t}{2RF}}\right),$$

where Q represents a charge amount per half wave of the alternating current signal, R represents a resistance component of the conductor, C represents a capacitance component of the conductor, E represents a peak voltage of the alternating current signal, f represents the frequency of the alternating current signal, and t represents time.

2. The vision regeneration assisting apparatus according to claim 1, wherein the electrical stimulation pulse signal is generated based on the extracted electrical stimulation pulse signal data.

3. The vision regeneration assisting apparatus according to claim 2, wherein the conductor includes a platinum or a platinum alloy, and
    the charge amount per the half wave of the alternating current signal is determined so that the charge amount per unit area discharged from the conductor when the conductor is exposed and wetted by the bodily fluid is equal to or less than 400 μC/cm$^2$.

* * * * *